(12) United States Patent
Holland et al.

(10) Patent No.: US 9,453,430 B2
(45) Date of Patent: Sep. 27, 2016

(54) METHOD FOR TRACKING TURBINE BLADE CREEP

(71) Applicant: Siemens Energy, Inc., Orlando, FL (US)

(72) Inventors: Stephen Erick Holland, Oviedo, FL (US); Chad W. Heinrich, Oviedo, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 392 days.

(21) Appl. No.: 14/221,626

(22) Filed: Mar. 21, 2014

(65) Prior Publication Data
US 2015/0267553 A1 Sep. 24, 2015

(51) Int. Cl.
| F01D 5/00 | (2006.01) |
| F01D 21/00 | (2006.01) |
| G01N 3/56 | (2006.01) |
| G01N 3/60 | (2006.01) |
| G01B 11/16 | (2006.01) |

(52) U.S. Cl.
CPC ............ *F01D 21/003* (2013.01); *F01D 5/005* (2013.01); *G01B 11/20* (2013.01); *G01N 3/56* (2013.01); *G01N 3/60* (2013.01); *Y02E 10/723* (2013.01)

(58) Field of Classification Search
USPC .................. 116/208, 216; 252/408.1; 374/57; 416/241 R, 224, 61; 73/762
See application file for complete search history.

(56) References Cited

U.S. PATENT DOCUMENTS

| 3,638,495 | A | * | 2/1972 | Sessler | G01K 3/04 374/103 |
| 3,999,946 | A | * | 12/1976 | Patel | G01N 31/229 252/962 |
| 4,015,465 | A | * | 4/1977 | Scott | G01B 11/18 116/212 |
| 4,715,988 | A | * | 12/1987 | Colin | G01N 23/223 252/408.1 |
| 5,053,339 | A | * | 10/1991 | Patel | G01N 31/229 116/206 |
| 8,012,375 | B2 | | 9/2011 | Hughes | |
| 8,695,445 | B2 | * | 4/2014 | Laurer | F01D 5/12 116/208 |
| 8,784,056 | B2 | * | 7/2014 | Willett, Jr. | F01D 21/003 415/118 |
| 2009/0293596 | A1 | * | 12/2009 | Ehehalt | F01D 17/16 73/112.02 |
| 2009/0301382 | A1 | * | 12/2009 | Patel | G01D 3/10 116/201 |
| 2011/0116906 | A1 | * | 5/2011 | Smith | B64C 11/205 415/1 |
| 2013/0174656 | A1 | * | 7/2013 | MacKelvie | F16D 66/02 73/121 |
| 2014/0092934 | A1 | * | 4/2014 | Isobe | G01N 25/72 374/4 |
| 2015/0184536 | A1 | * | 7/2015 | Panicker | F01D 21/003 416/1 |
| 2015/0346057 | A1 | * | 12/2015 | Ward, Jr. | C23C 4/11 73/762 |

* cited by examiner

Primary Examiner — R. K. Arundale

(57) ABSTRACT

A method for inspecting a turbine blade of a turbine. The method includes operating the turbine and providing a plurality of ablative material strips on the turbine blade. Each strip is fabricated from a common base material and is configured to ablate after exposure to a corresponding predetermined temperature for a corresponding predetermined time period Ablation of a strip indicates a corresponding amount of creep has occurred in the blade. In addition, the method includes visually inspecting the strips at predetermined intervals to determine whether one or more of the strips is ablated.

20 Claims, 2 Drawing Sheets

FIG. 3
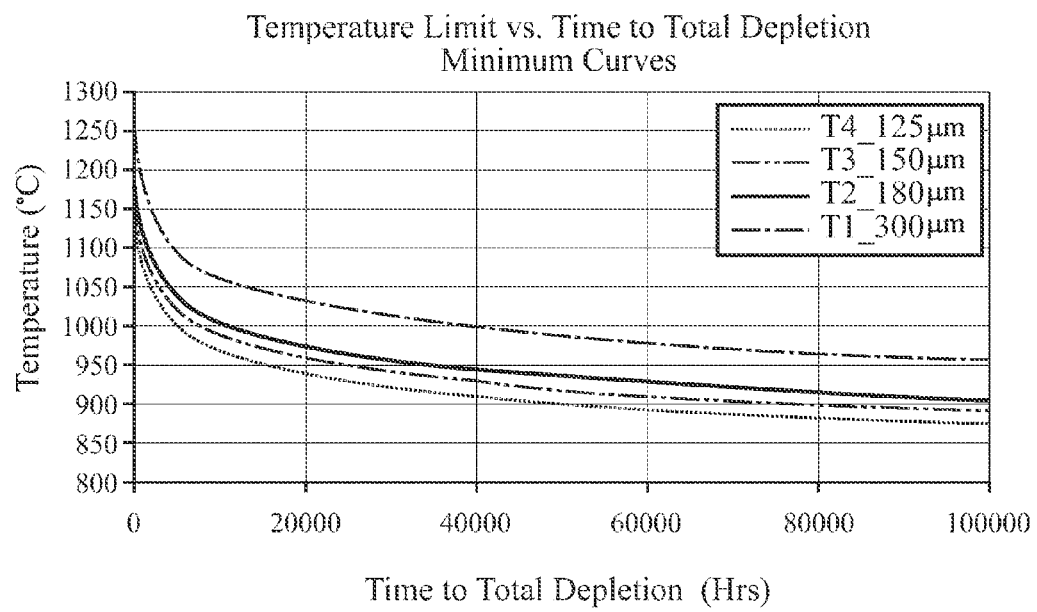
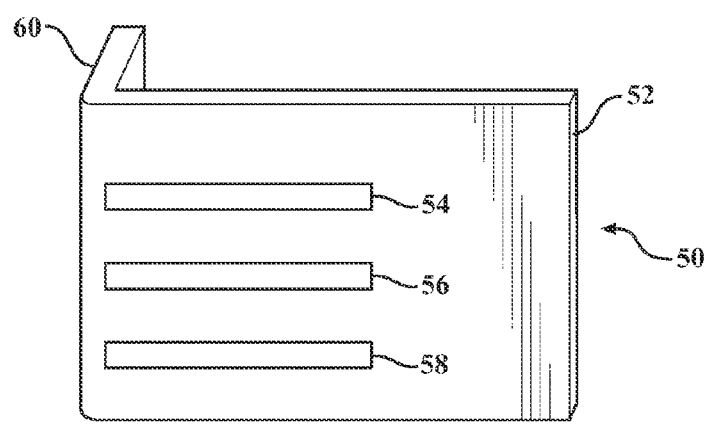
FIG. 4

ID OF THE INVENTION

This invention relates to the tracking of turbine blade creep, and more particularly, to a method for inspecting a turbine blade of a turbine which includes providing an ablative material strip on the turbine blade.

BACKGROUND OF THE INVENTION

Many components of a turbine, such as the turbine blades, have an operational life beyond which maintenance or replacement is required An important factor in determining the operational life of turbine blades is the creep rupture life that is calculated for the turbine blades. The calculation of creep rupture life is dependent on several parameters and includes predictions for the mechanical stress levels and temperature that the turbine blades will be exposed to during operation and the duration of the stress levels and temperature. Alternatively, a turbine blade may be one-time tested under specific operating conditions to establish the parameters for determining operational life.

However, the actual operating conditions that the turbine blades are exposed to, such as the temperature, may vary significantly from the parameters initially used to calculate creep rupture life or test the turbine blades Further, it is difficult to inspect the blades to determine how much creep exists when the turbine is assembled and in operation As a result, the turbine blades are replaced based on a conservative calculation for the creep rupture life in order to avoid catastrophic turbine failure. This can result in premature replacement of turbine blades thus increasing long term maintenance costs.

SUMMARY OF THE INVENTION

A method for inspecting a turbine blade of a turbine is disclosed. The method includes operating the turbine and providing at least one ablative material strip on the turbine blade The strip is configured to ablate after exposure to a predetermined temperature for a predetermined time period. In addition, the method includes visually inspecting the strip at predetermined intervals to determine whether the strip is ablated. The strip may be configured such that ablation of the strip indicates that a creep rupture limit for the blade is being approached Further, the strip may be configured such that non-ablation of the strip indicates that additional operational life for the blade is available

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein FIG. 3 depicts temperature limit vs. time to total depletion curves for bond coatings having different thicknesses.

FIG. 4 depicts a mask for forming the first, second and third strips

DETAILED DESCRIPTION OF THE INVENTION

Figure 1:
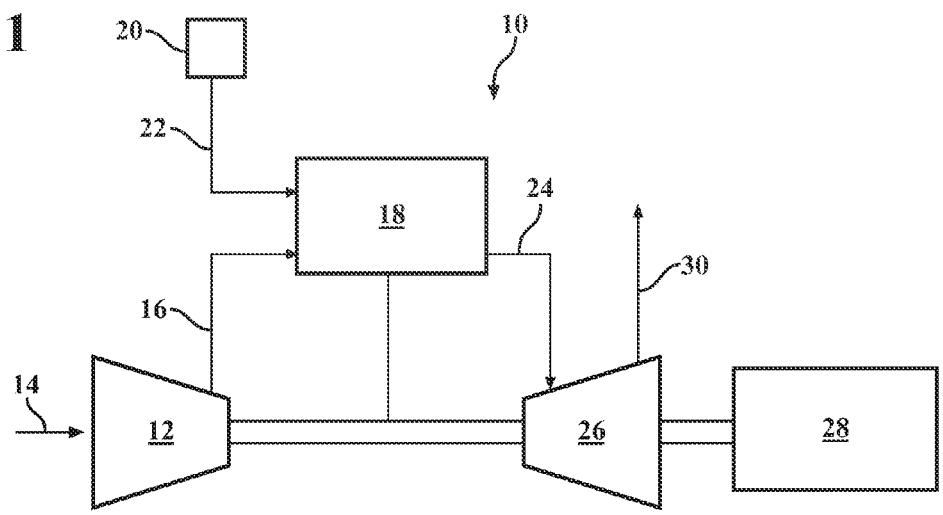
FIG. 1 is a schematic depiction of a gas turbine

In the following detailed description of the preferred embodiment, reference is made to the accompanying drawings that form a part hereof, and in which is shown by way of illustration, and not by way of limitation, a specific preferred embodiment in which the invention may be practiced It is to be understood that other embodiments may be utilized and that changes may be made without departing from the spirit and scope of the present invention Referring to FIG. 1, a gas turbine 10 is schematically shown The turbine 10 includes a compressor 12 which draws in ambient air 14 and delivers compressed air 16 to a combustor 18. A fuel supply 20 delivers fuel 22 to the combustor 18 where it is combined with the compressed air and the fuel is burned to produce high temperature combustion gas 24. The combustion gas 24 is expanded through a turbine section 26 which includes a series of rows of stationary vanes and rotating turbine blades The combustion gas 24 causes the blades to rotate to produce shaft horsepower for driving the compressor 12 and a load, such as an electrical generator 28 The expanded gas 30 is either exhausted to the atmosphere directly, or in a combined cycle plant, may exhausted to atmosphere through a heat recovery steam generator.

Figure 2:
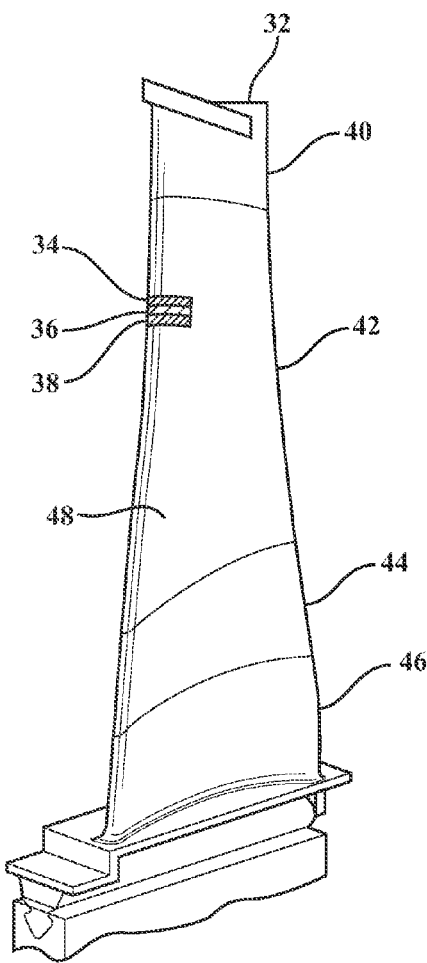
FIG. 2 shows an exemplary turbine blade which includes first, second and third ablative material strips in accordance with the invention

Referring to FIG. 2, an exemplary turbine blade 32 from the turbine section 26 is shown. During operation of the turbine 10, the blade 32 is subjected to stress levels primarily due to the constant rotation of the blade 32 in the turbine section 26 and to high temperatures resulting from exposure to the combustion gas 24 The amount of creep that occurs in the blade 32 is dependent on several parameters including the stress levels and temperature that the blade 32 is actually exposed to during operation along with the duration of the stress levels and temperature In accordance with an aspect of the invention, the blade 32 can include at least one ablative strip to provide an indication of a temperature related condition to which the blade 32 has been exposed. In the illustrated embodiment, the blade 32 includes first 34, second 36 and third 38 ablative material strips in accordance with the invention which are exposed to the same temperatures as the blade 32. The first 34, second 36 and third 38 strips are configured to completely ablate after exposure to first, second and third temperatures for first, second and third predetermined periods of time, respectively, during operation of the turbine Ablation of either of the first 34, second 36 and third 38 strips, or a combination of the strips 34, 36, 38, indicates that a corresponding duration of exposure to a threshold temperature has occurred in the blade 32. As the stress level in the blade is fairly uniform and predictable, the duration of exposure to a threshold temperature is indicative of creep in the blade It has been determined that monitoring creep of a single blade, such as blade 32 shown in FIG. 2, is sufficiently indicative of the creep status of the remaining blades in the turbine section 26. Thus, a determination that the blade 32 should be replaced also indicates that the remaining blades in the turbine section 26 should be replaced. Alternatively, a plurality of blades may include the first 34, second 36 and third 38 strips.

Although three strips 34, 36, 38 are shown, it is noted that additional or fewer strips may be used in order to accommodate additional exposure temperatures and periods of time Alternatively, a single strip may be used in order to indicate that a predetermined amount of creep has occurred after exposure to a predetermined temperature. For example, the single strip may be configured to ablate when a creep rupture limit for the blade is being approached after exposure to a predetermined temperature In one embodiment, the first 34, second 36 and third 38 strips each have a rectangular shape Referring to Table 1, exemplary parameters for the first 34, second 36 and third 38 strips are shown. In particular, Table 1 lists the maximum operational life of a blade (i.e. "MAX BLADE OPERATIONAL LIFE") after exposure to operating temperatures (i.e "OPERATING TEMPERATURE") of approximately 830C, 840C and 850C, respectively. Further, Table 1 lists the approximate time periods after which the first 34, second 36 and third 38 strips become ablated (i.e. "TIME FOR STRIP ABLATION") after exposure to operating temperatures of approximately 830C, 840C and 850C, respectively

TABLE 1

| STRIP | OPERATING TEMPERATURE (° C.) | MAX BLADE OPERATIONAL LIFESPAN (HRS) | TIME FOR STRIP ABLATION (HRS) |
|---|---|---|---|
| FIRST STRIP 34 | 830 | 100,000 | 75,000 |
| SECOND STRIP 36 | 840 | 50,000 | 25,000 |
| THIRD STRIP 38 | 850 | 25,000 | 12,500 |

During operation, a turbine is typically inspected at periodic intervals such as 12,500 operating hour time intervals In accordance with the invention, a determination during an inspection that either of the first 34, second 36 or third 38 strips is ablated indicates that the blades in the turbine section 26 should be replaced due to an undesirable amount of creep that has occurred in the blades Conversely, a determination during an inspection that all of the strips 34, 36, 38 are not ablated indicates that negligible creep has occurred in the blade 32. When this occurs, it is considered safe to continue to use the current blades for at least another 12,500 hours (i.e. until the next inspection) Continuous inspection of the blade at 12,500 hour time intervals enables a periodic determination of whether all of the strips 34, 36, 38 are still intact (i.e. not ablated). This enables continued use of the blades beyond that which is initially calculated for avoiding catastrophic turbine failure. As a result, premature blade replacement and associated costs can be avoided.

The turbine is configured such that an inspector is able to visually inspect the blade 32 and determine the status of the first 34, second 36 and third 38 strips (i.e. whether the strips are ablated or non-ablated) without disassembly of the turbine section 26. In one embodiment, the first 34, second 36 and third 38 strips are configured such that the strips ablate at multiples of 12,500 hours (i.e., at 75,000, 25,000 and 12,500 hours as shown in Table 1) Thus, any strip ablation that occurs will generally coincide with a scheduled inspection.

For example, if an inspection determines that the first strip 34 is ablated, this indicates that the blades in the turbine section 26 have been exposed to a temperature of approximately 830C for approximately 75,000 hours. Referring to Table 1, this indicates that the blades have an additional approximate 25,000 hours of operating life remaining until the maximum blade operational life of 100,000 hours is reached. In one embodiment, the blades are replaced after it is first determined that the first strip 34 is ablated although approximately 25,000 hours of operational life remain to ensure that blade failure does not occur.

In addition, if an inspection determines that the second strip 36 is ablated, this indicates that the blades have been exposed to a temperature of approximately 840C for approximately 25,000 hours Referring to Table 1, this indicates that the blades have an additional approximate 25,000 hours of operational life remaining until the maximum blade operational life of 50,000 hours is reached. The blades are replaced after it is first determined that the second strip 36 is ablated although approximately 25,000 hours of operational life remain to ensure that blade failure does not occur.

Further, if an inspection determines that the third strip 38 is ablated, this indicates that the blades have been exposed to a temperature of approximately 850C for approximately 12,500 hours Referring to Table 1, this indicates that the blades have an additional approximate 12,500 hours of operational life remaining until the maximum blade operation life of 25,000 hours is reached. The blades are replaced after it is first determined that the third strip 38 is ablated although approximately 12,500 hours of operational life remain to ensure that turbine blade failure does not occur.

The first 34, second 36 and third 38 strips are located in a portion of the blade 10 which has been identified as a risk area for creep. It has been determined that the risk area for creep is located where a high temperature area of the blade 32 coincides with high stress area of the blade 32. The high temperature and high stress areas of the blade 32 may be determined by computer modeling or other design techniques FIG. 2 depicts exemplary first 40, second 42, third 44 and fourth 46 temperature regions of the blade 32. For purposes of illustration, the second region 42 in FIG. 2, located in an upper portion of the blade 32, is depicted as having the highest temperature. Further, the second region 42 is determined to have the highest stress level. Thus, the first 34, second 36 and third 38 strips are located in the second region 42 as depicted in FIG. 2. It is noted that the location of the first 34, second 36 and third 38 strips is dependent on the design of the particular blade being used and thus may vary from that shown in FIG. 2. For example, the high temperature and high stress areas of a blade, due to its design, may be located in a middle or lower portion of the blade. Accordingly, the first 34, second 36 and third 38 strips would then be located in a corresponding middle or lower portion of the blade 32. The first 34, second 36 and third 38 strips may be located near an edge 48 of the blade 32 as shown in FIG. 2 or away from the edge 48. In addition, the first 34, second 36 and third 38 strips may be adjacent each other or spaced apart from each other.

The first 34, second 36 and third 38 strips may be formed from a common base material that ablates when exposed to a predetermined temperature. Other materials may then be added to the base material that would either raise or lower the ablation temperature of the combined materials as desired so that the first 34, second 36 and third 38 strips completely ablate after exposure to first, second and third temperatures for the first, second and third predetermined periods of time, respectively, during operation of the turbine.

Alternatively, the first 34, second 36 and third 38 strips may be formed from an existing coating that is already used on the blade 32 For example, a bond coating is frequently applied on turbine blades in order to protect the blade from corrosion and oxidation of the blade material Contaminants or other materials may then be added to the bond coating that would either raise or lower the ablation temperature as desired to form the first 34, second 36 and third 38 strips. An example of a bond coating that may be used is Siemens SC2464 coating. Another type of coating which may be used to form the first 34, second 36 and third 38 strips may be a thermal barrier coating of the type used to thermally insulate the blade material from the hot environment within the turbine section 26.

In another embodiment, the first 34, second 36 and third 38 strips may be formed by increasing the thickness of a section of the bond or thermal barrier coatings, or a combination of the bond and thermal barrier coatings Referring to FIG. 3, temperature limit vs time to total depletion curves for a typical bond coating having thicknesses of 300 μm, 180 μm, 150 μm and 125 μm, identified as T1, T2, T3 and T4, respectively, are shown. As can be seen from FIG. 3, the temperature limit for a thinner coating such as T4 is lower than that of thicker coating such as T1. The bond coating characteristics regarding temperature, thickness and time to total depletion can be used to form the first 34, second 36 and third 38 strips Thus, the first strip 34 may be fabricated from a bond coating having a first thickness having an associated first ablation temperature. In addition, the second strip 36 may have a second thickness, larger than the first thickness, which is associated with a second ablation temperature higher than the first ablation temperature. Further, the third strip 38 may have a third thickness, larger than the second thickness, which is associated with a third ablation temperature higher than the second temperature.

The first 34, second 36 and third 38 strips may each be formed on the blade 32 by using a plasma spray technique in conjunction with a mask Referring to FIG. 4, a mask 50 for forming the first 34, second 36 and third 38 strips is shown The mask 50 includes a front plate 52 having first 54, second 56 and third 58 elongated slots which are sized for forming the first 34, second 36 and third 38 strips. The mask 50 also includes a side plate 60 which abuts against the edge 48 of the blade 32. The side plate 60 serves to position the first 54, second 56 and third 58 slots in a desired position relative to the edge 48

While particular embodiments of the present invention have been illustrated and described, it would be obvious to those skilled in the art that various other changes and modifications can be made without departing from the spirit and scope of the invention It is therefore intended to cover in the appended claims all such changes and modifications that are within the scope of this invention.

What is claimed is:

1. A method for inspecting a turbine blade of a turbine, comprising:
   operating the turbine;
   providing at least one ablative material strip on the turbine blade, wherein the strip is configured to ablate after exposure to a predetermined temperature for a predetermined time period and wherein ablation of the strip indicates a corresponding amount of creep has occurred in the blade; and
   visually inspecting the strip to determine whether the strip is ablated.

2. The method according to claim 1, further including providing the strip in an area of the blade having stress and temperatures resulting from exposure to a combustion gas.

3. The method according to claim 1, wherein first, second and third strips are used.

4. The method according to claim 3, wherein the first strip ablates after exposure to a temperature of 830C for 75,000 hours, the second strip ablates after exposure to a temperature of 840C for 25,000 hours and the third strip ablates after exposure to a temperature of 850C for 12,500 hours.

5. The method according to claim 1, wherein ablation of the strip indicates that a creep rupture limit is being approached.

6. The method according to claim 1, wherein non-ablation of the strip indicates that a creep rupture limit is not being approached.

7. The method according to claim 1, wherein the strip is located in an upper portion of the blade.

8. The method according to claim 1, further including fabricating the strip from a base material to which contaminants are added in order to obtain a desired ablation temperature for the strip.

9. The method according to claim 8, wherein the base material is a bond coating material.

10. A method for inspecting a turbine blade of a turbine, comprising:
    operating the turbine;
    providing a plurality of ablative material strips on the turbine blade, wherein each strip is configured to ablate after exposure to a corresponding predetermined temperature for a corresponding predetermined time period and wherein ablation of a strip indicates a corresponding amount of creep has occurred in the blade; and
    visually inspecting the strips at predetermined intervals to determine whether one or more of the strips is ablated.

11. The method according to claim 10, further including providing the strips in an area of the blade having stress and temperatures resulting from exposure to a combustion gas.

12. The method according to claim 10, wherein the first strip ablates after exposure to a temperature of 830C for 75,000 hours, the second strip ablates after exposure to a temperature of 840C for 25,000 hours and the third strip ablates after exposure to a temperature of 850C for 12,500 hours.

13. The method according to claim 10, wherein ablation of any of the strips indicates that a creep rupture limit is being approached.

14. The method according to claim 10, wherein non-ablation of all of the strip indicates that a creep rupture limit is not being approached.

15. The method according to claim 10, wherein the strips are located in an upper portion of the blade.

16. The method according to claim 10, further including fabricating the strips from a common base material.

17. The method according to claim 16, wherein the base material is a bond coating material.

18. A method for inspecting a turbine blade of a turbine, comprising:
    operating the turbine;
    providing first, second and third ablative material strips on the turbine blade, wherein each strip is fabricated from a common base material and is configured to ablate after exposure to a corresponding predetermined temperature for a corresponding predetermined time period and wherein ablation of a strip indicates a corresponding amount of creep has occurred in the blade; and
    visually inspecting the strips at predetermined intervals to determine whether one or more of the strips is ablated.

19. The method according to claim 18, wherein ablation of any of the strips indicates that a creep rupture limit is being approached.

20. The method according to claim 18, wherein non-ablation of all of the strip indicates that a creep rupture limit is not being approached.

* * * * *